United States Patent [19]

Leung et al.

[11] Patent Number: 5,194,660
[45] Date of Patent: Mar. 16, 1993

[54] PROCESSES FOR PRODUCING CARBAMATES AND ISOCYANATES

[75] Inventors: Tak W. Leung; Bernard D. Dombek, both of Charleston, W. Va.

[73] Assignee: Union Carbide Chemicals & Plastics Technology Corporation, Danbury, Conn.

[21] Appl. No.: 631,962

[22] Filed: Dec. 21, 1990

[51] Int. Cl.$^5$ .................................... C07C 269/04
[52] U.S. Cl. ...................................... 560/24; 560/25; 560/27; 560/29; 560/30; 560/31; 560/32; 560/33; 560/115; 560/157; 560/158; 560/159; 560/160; 560/161; 560/162; 560/163; 560/165; 560/166; 560/167; 560/341; 562/555

[58] Field of Search ............. 560/157, 24, 115, 158, 560/167, 341; 562/555

[56] References Cited

U.S. PATENT DOCUMENTS

| | | | |
|---|---|---|---|
| 3,696,263 | 10/1972 | Wacher | 313/108 D |
| 3,895,054 | 7/1975 | Zajacek et al. | 260/471 |
| 3,956,360 | 5/1976 | Zajacek et al. | 260/471 |
| 3,962,302 | 6/1976 | Rosenthal et al. | 560/24 |
| 3,993,489 | 11/1976 | Heimsch et al. | 96/77 |
| 3,993,685 | 11/1976 | Zajacek et al. | 260/471 |
| 4,115,445 | 9/1978 | Hearsey | 260/553 |
| 4,151,208 | 4/1979 | Pretzer et al. | 260/601 |
| 4,170,708 | 10/1979 | Hirai et al. | 560/24 |
| 4,186,269 | 1/1980 | Hirai et al. | 560/25 |
| 4,202,992 | 5/1980 | Coltrin et al. | 568/575 |
| 4,236,016 | 11/1980 | Scholl et al. | 560/24 |
| 4,242,520 | 12/1980 | Moy | 560/24 |
| 4,258,201 | 3/1981 | Moy | 560/24 |
| 4,266,070 | 5/1981 | Moy | 560/24 |
| 4,267,353 | 5/1981 | Scholl et al. | 560/24 |
| 4,271,038 | 6/1981 | Pesa et al. | 252/428 |
| 4,290,970 | 9/1981 | Merger et al. | 560/24 |
| 4,297,501 | 10/1981 | Becker et al. | 560/24 |
| 4,339,592 | 7/1982 | Becker et al. | 560/25 |
| 4,386,033 | 5/1983 | König et al. | 560/24 |
| 4,386,087 | 5/1983 | Lavallee | 424/245 |
| 4,388,238 | 6/1983 | Heitkämper et al. | 560/24 |
| 4,439,616 | 3/1984 | Singh et al. | 560/24 |
| 4,469,882 | 9/1984 | Takeuchi et al. | 560/25 |
| 4,474,978 | 10/1984 | Drent et al. | 560/25 |
| 4,480,110 | 10/1984 | Heitkämper et al. | 560/24 |
| 4,490,551 | 12/1984 | Scholl et al. | 560/25 |
| 4,552,818 | 11/1985 | Wong | 428/447 |
| 4,568,435 | 2/1986 | Shelnutt | 204/157.52 |
| 4,568,761 | 2/1986 | Henderson, Jr. | 560/24 |
| 4,582,923 | 4/1986 | Stammann et al. | 560/24 |
| 4,587,056 | 5/1986 | Fukuoka et al. | 560/341 |
| 4,600,793 | 7/1986 | Grate et al. | 560/24 |
| 4,621,149 | 11/1986 | Fukuoka et al. | 560/24 |
| 4,687,872 | 8/1987 | Grate et al. | 560/24 |
| 4,694,097 | 9/1987 | Alper et al. | 560/24 |
| 4,822,899 | 4/1989 | Groves et al. | 549/533 |
| 4,879,410 | 11/1989 | Singh et al. | 560/24 |

OTHER PUBLICATIONS

Maddinelli et al, *Journal of Molecular Catalysis*, 39 (1987) 71–77.

Medforth et al, "Tetracycloalkenyl-Meso-Tetraphenylporphyrins as Models for the Effect of Non--Planarity on the Light Absorption Properties of Photosynthetic Chromophores", Tetrahedron Letters, vol. 31, No. 26, pp. 3719–3722, 1990.

Yoshida et al, "A New Synthesis of Cyclic Ureas, Cyclic Urethanes, and a Quinazolinedione, Selenium-Assisted Carbonylation of Aromatic Amines with Carbon Monoxide", The Chemical Society of Japan, 1987, vol. 60, pp. 1793–1799.

Ganeshpure et al, "Oxidation of Phenols with Molecular Oxygen Catalysed by [N,N'-Bis(2'-Pyridinecarboxamido)-1,2-Benzene]Cobalt (II), Chelate", Tetrahedron Letters, vol. 30, No. 43, pp. 5929–5932, 1989.

Benedini, et al, "The Bis (salicylaldehyde) ethylene diimine Cobalt (II)-Catalyzed Oxidative Carbonylation of Primary and Secondary Amines", Journal of Molecular Catalysis, 34 (1986) 155–161.

Kugimiya et al, "Novel Liquid Crystals of Tetraphenylporphyrin Derivatives", Tetrahedron Letters, vol. 31, No. 22, pp. 3157–3160, 1990.

*Primary Examiner*—José G. Dees
*Assistant Examiner*—B. Frazier
*Attorney, Agent, or Firm*—S. H. Hegedus

[57] ABSTRACT

Processes for producing carbamates comprise contacting a first reactant selected from primary amine components, secondary amine components, urea components and mixtures thereof; carbon monoxide; at least one organic hydroxyl component and at least one oxygen-containing oxidizing agent in the presence of a catalyst composition comprising at least one metal macrocyclic complex, preferably in the further presence of a halogen component.

7 Claims, No Drawings

PROCESSES FOR PRODUCING CARBAMATES AND ISOCYANATES

BACKGROUND OF THE INVENTION

This invention relates to processes for producing carbamates using certain metal-containing catalyst compositions. More particularly, the invention relates to processes for producing carbamates by reacting amines and/or ureas, carbon monoxide, organic hydroxyl components and an oxygen-containing oxidizing agent in the presence of certain metal-containing catalyst compositions.

Carbamates, or urethanes, are useful, for example, in producing isocyanates and as pesticides. The desired isocyanate can often be obtained by thermally decomposing the carbamate. A number of different methods have been suggested for producing carbamates.

Zajacek et al U.S. Pat. Nos. 3,895,054 and 3,956,360 disclose a process for preparing urethanes by reacting an organic hydroxyl compound with carbon monoxide and a nitrogenous organic compound, such as an organic nitro compound, in the presence of a catalyst containing sulfur and/or selenium and/or tellurium and at least one of base and water. A number of patents disclose the use of selenium and/or sulfur and/or tellurium as a catalyst for the conversion of amines to carbamates and ureas, which can be used as precursors to carbamates. See, for example, Hirai et al U.S. Pat. No. 4,170,708; Scholl et al U.S. Pat. Nos. 4,236,016; 4,267,353; and 4,490,551; and Moy U.S. Pat. Nos. 4,242,520 and 4,258,201.

Various processes based on the use of platinum group metal catalysts to promote the formation of urethanes/carbamates from organic hydroxyl compounds, carbon monoxide, organic nitrogen compounds, such as organic nitrocompounds or amines, and possibly an oxygen-containing oxidizing agent have been suggested. See, for example, Zajacek et al U.S. Pat. No. 3,993,685; Becker et al U.S. Pat. Nos. 4,297,501 and 4,339,592; Stammann et al U.S. Pat. No. 4,582,923; Hirai et al U.S. Pat. No. 4,186,269, Fukuoka et al U.S. Pat. No. 4,621,149; and Grate et al U.S. Pat. No. 4,600,793. Moy U.S. Pat. No. 4,266,070 discloses a process for producing urethanes by reacting an organic primary or secondary amine, in the absence of reactive oxygen, with carbon monoxide and an organic hydroxyl component using a catalyst of carbonyls of cobalt, molybdenum, titanium, rhodium, iron and nickel. In many instances, a co-catalyst component is required. Also, the catalysts often tend to become deactivated, or even decompose, at reaction conditions. Thus, if the catalytically active metal is to be reused, it may have to be recovered from the product and reactivated, or even reconstituted, before such reuse. Catalyst compositions which do not require co-catalysts and/or which have enhanced stability at reaction conditions would clearly be advantageous.

Pretzer et al U.S. Pat. No. 4,151,208 discloses a process for producing acetaldehyde from methanol, hydrogen and carbon monoxide using a cobalt (II) meso-tetraaromaticporphine catalyst and an iodine promoter. Pesa et al U.S. Pat. No. 4,271,038 discloses a process for producing aldehydes by the reaction of carbon monoxide, hydrogen and olifinically unsaturated compounds in the presence of a catalyst of cobalt carbonyl and porphyrin promoter ligand. Neither of these two patents discloses or even suggests carbamate production.

Relatively recent work reported by Italian researchers has disclosed that anilines can be oxidized to azobenzenes in methanol or methylene chloride solution using dioxygen as the oxidant and bis (salicylaldehyde) ethylenediimine cobalt (II) as catalyst. In the presence of carbon monoxide, isocyanates, urethanes and ureas are also obtained. See: Benedini, et al, "The Bis (salicylaldehyde) ethylene diimine Cobalt (II)-catalyzed Oxidative Carbonylation of Primary and Secondary Amines", Journal of Molecular Catalysis, 34 (1986) 155–161; and Maddinelli, et al, "The Bis (salicylaldehyde) ethylenediimine Cobalt II - catalyzed Oxidative Carbonylation of 1-Adamantylamine in Alcohol: A Study for Optimizing Carbamate Formation", Journal of Molecular Catalysis, 39 (1987) 71–77. No other catalysts, and no reaction promoters, are disclosed or suggested by this work.

There continues to be a need for a process for producing carbamates.

SUMMARY OF THE INVENTION

New processes for producing carbamates have been discovered. The present processes use catalyst compositions capable of promoting the conversion of both aliphatic and aromatic amines, as well as urea components, to carbamates in relatively high yields in reactions involving the amine and/or the urea component, carbon monoxide, an organic hydroxyl component and an oxygen-containing oxidizing agent. The present catalyst compositions are substantially resistant to oxidative destruction at reaction conditions so that such compositions can be used repeatedly, thus lowering the cost of producing the carbamates. In addition, the catalyst compositions are preferably soluble in the liquid portion of the reaction mixture which allows very intimate catalyst/reactant contacting. The soluble catalyst can be easily separated from the product carbamate. The carbamates produced can be converted in high yields to isocyanates, if desired, for example, by thermolysis.

In one embodiment, a process for producing a carbamate is provided which comprises contacting a first reactant, carbon monoxide, at least one organic hydroxyl component and at least one oxygen-containing oxidizing agent in the presence of a catalyst composition in an amount effective to promote the formation of a carbamate at conditions effective to form a carbamate. The first reactant is selected from primary amine components, secondary amine components, urea components and mixtures thereof. The catalyst composition comprises at least one metal macrocyclic complex. In one particularly useful embodiment, this complex is other than bis (salicylaldehyde) ethylenediimine cobalt (II). The present contacting preferably takes place in the presence of at least one halogen component in an amount effective to facilitate the formulation of the carbamate.

DETAILED DESCRIPTION OF THE INVENTION

The present invention provides carbamates from the reaction of a first reactant, carbon monoxide, at least one organic hydroxyl component and at least one oxygen-containing oxidizing agent. The reactants are contacted, e.g., chemically reacted, in the presence of a certain defined catalyst composition, and preferably a halogen component, at conditions effective to form a carbamate. The first reactant is selected from primary amine components, secondary amine components, urea components and mixtures thereof. The catalyst composition is selected from metal macrocyclic complexes capable of promoting the formation of the carbamate and mixtures thereof.

The catalyst composition is present in an amount effective to promote the formation of the desired carbamate at the contacting conditions. The presently useful catalyst compositions comprise one or more metal macrocyclic complexes.

The term "complex" as used herein and in the claims means a coordination compound formed by the union of one or more electronically rich molecules or atoms capable of independent existence with one or more electronically poor molecules or atoms, each of which is also capable of independent existence. The presently useful macrocyclic ligands are relatively large ring compounds with structures so that two or more, preferably at least four, donor atoms can bind or coordinate to a single metal entity, for example, a metal ion, at two or more, preferably at least four, metal coordination sites. Examples of donor atoms include nitrogen, oxygen, sulfur, phosphorus and the like and mixtures thereof.

Macrocyclic complexes have a marked kinetic inertness both to the formation of the complexes from the ligand and the metal ion, and to the extrusion or withdrawal of the metal ion from the complex. Such complexes stabilize metal oxidation states, such as Cu (III) and Ni (III), which are not normally attainable. In addition, the macrocyclic complexes have high thermodynamic stability, for example, relative to nonmacrocyclic complexes.

The presently useful metal macrocyclic complexes are preferably soluble in the liquid phase in which the present contacting preferably occurs at the contacting conditions. This feature provides very effective and intimate contact between the catalyst composition and the reactants so that the desired carbamate formation reaction is facilitated. Preferably, the metal macrocyclic complex or complexes are redox cyclable at the contacting conditions. That is, the metal ion included in the complex preferably can cycle between at least two oxidation states at the conditions of the present contacting. Without wishing to limit the invention to any particular theory of operation, it is believed that such redox cyclable complexes are particularly useful in promoting carbamate formation where the active catalytic species includes the metal ion in the higher or highest oxidation state. Thus, the metal macrocyclic complex may be introduced into the contacting zone with the metal ion in a relatively low oxidation state. At the contacting conditions, the active catalytic species is formed and/or maintained. If the metal ion is reduced to a relatively low oxidation state, the contacting conditions are such as to oxidize the metal ion to the higher or highest, catalytically active, oxidation state.

The presently useful metal macrocylic complexes preferably are substantially resistant to oxidation. That is, such complexes are preferably substantially resistant to oxidative destruction at the conditions of the contacting. This feature facilitates the repeated reuse of the present catalyst compositions.

The presently useful metal macrocyclic complexes preferably include at least one metal selected from the metals of Group IIIa to Va, Groups Ib to VIIb and Group VIII of the Periodic Table (References to the Periodic Table herein shall be to that published by the Chemical Rubber Company, Cleveland, Ohio, in CRC Handbook of Chemistry and Physics, 46th Edition, inside back cover.) More preferably, the metal macrocyclic complexes include at least one of copper, zinc, mercury, thallium, tin, titanium, arsenic, antimony, bismuth, vanadium, chromium, molybdenum, tungsten, manganese, iron, cobalt, nickel and the platinum group metals, i.e., platinum, palladium, indium, rhodium, ruthenium and osmium. Particularly useful results are achieved with metal macrocyclic complexes which include at least one of copper, cobalt, rhodium and palladium.

Any suitable metal macrocyclic complex may be employed in the present invention provided that it functions as described herein. Examples of useful metal macrocylic complexes include metal porphyrins, metal phthalocyanines, and metal complexes derived from Schiff base ligands.

The porphyrin ligands are porphine and derivatives of porphine. Porphine has the following formula

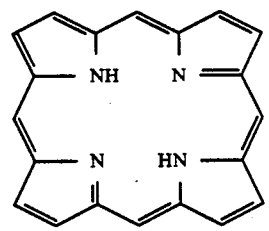

Among the porphine derivative ligands which are useful in this invention are those which can be represented by the following formula

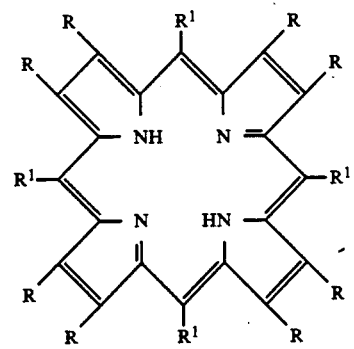

wherein each R is independently selected from the group consisting of:
 (1) H;
 (2) $C_{1-8}$ alkyl;
 (3) $-(CH_2)_y-COOT$, wherein y is 1–4 and T is H or a $C_{1-4}$ alkyl;
 (4) $C_{1-8}$ alcohol radical; and
 (5) $C_{1-8}$ alkene radical; and each $R^1$ is independently selected from the group consisting of:
 (1) H;
 (2) phenyl; and
 (3) phenyl substituted with one or more carboxy groups or $C_{1-4}$ alkyl groups or mixtures thereof.

Preferably each R is independently selected from the group consisting of H, $CH_3$, $C_2H_5$, $CH=CH_2$, $CH_2-COOH$, $(CH_2)_2-COOH$, $CH(OH)CH_3$ and $(CH_2)_2-COOCH_3$; and each $R^1$ is independently selected from the group consisting of H, phenyl and carboxyphenyl.

Examples of useful porphine derivative ligands include octaethylporphyrin which has the formula

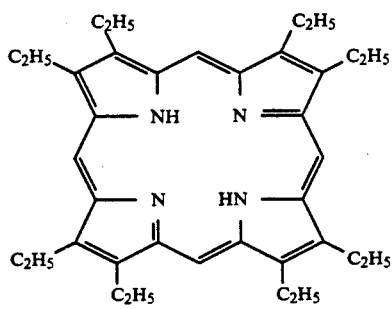

and meso-tetraphenylporphyrin which has the formula (4-XXV)

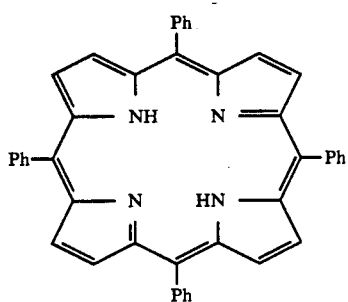

In the latter structure, the phenyl rings (Ph) are free to rotate. Although the most common form of coordination is that with the metal atom in the center of the plane and bound to 4 nitrogen atoms, porphyrins can act as bi-, tri-, tetra-, or hexadentate ligand in which the metal atom lies out of the $N_4$ plane.

carbonyls, acetylacetonates, alkyls, hydrides and the like.

The metal phthalocyanines can be obtained by interaction of phthalonitrile with metal halides, in which the metal ion acts as a template. Such metal phthalocyanines can be represented by the following structure.

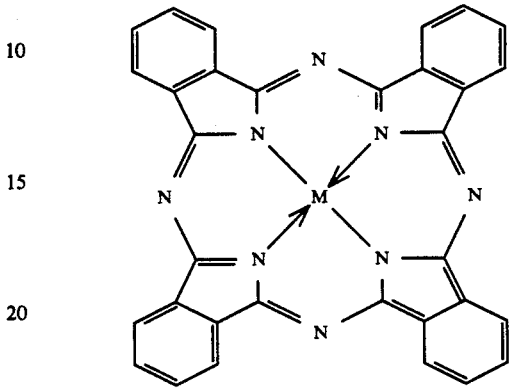

where M is a metal ion in the 2+ oxidation state. The metal ion in such phthalocyanine complexes may have an oxidation state other than 2+.

Schiff base ligands are very diverse and usually contain both nitrogen and oxygen donor atoms, although ligands with only nitrogen donor atoms or with nitrogen and sulfur donor atoms are known. A great variety of Schiff base ligands and Schiff base ligand metal complexes can be made by employing the Schiff base condensation reaction without, or with, a metal ion as a template, and with subsequent hydrogenation to obtain a saturated system. Examples of preparative reactions are as follows:

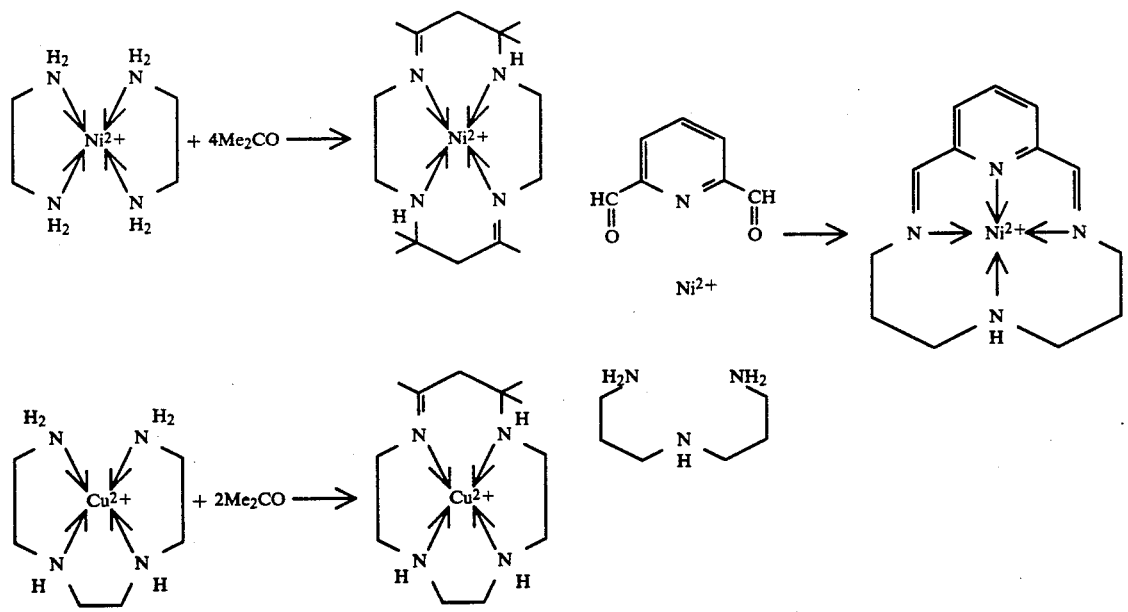

Complexes of synthetic porphyrins can be made by interaction of the ligand with a metal salt in a common solvent, such as dimethylformamide. Octaethylporphyrin is highly soluble in organic solvents, which meso-tetraphenylporphyrin is less so. Complexes can also be obtained by interaction of the porphyrin with metal A particularly useful Schiff base ligand is bis (salicylaldehyde) ethylenediamine which has the following formula:

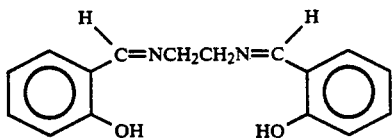

This is a bifunctional (two OH groups), tetradentate (2N, 2O) ligand. Other Schiff base ligands can be mono-, di- or tetrafunctional and can have denticities of 6 or more with various donor atom combinations. Complexes of un-ionized or partly ionized Schiff base ligands are also known. Further examples of metal complexes of Schiff base ligands which illustrate the formation of mononuclear, binuclear and polymeric species are as follows

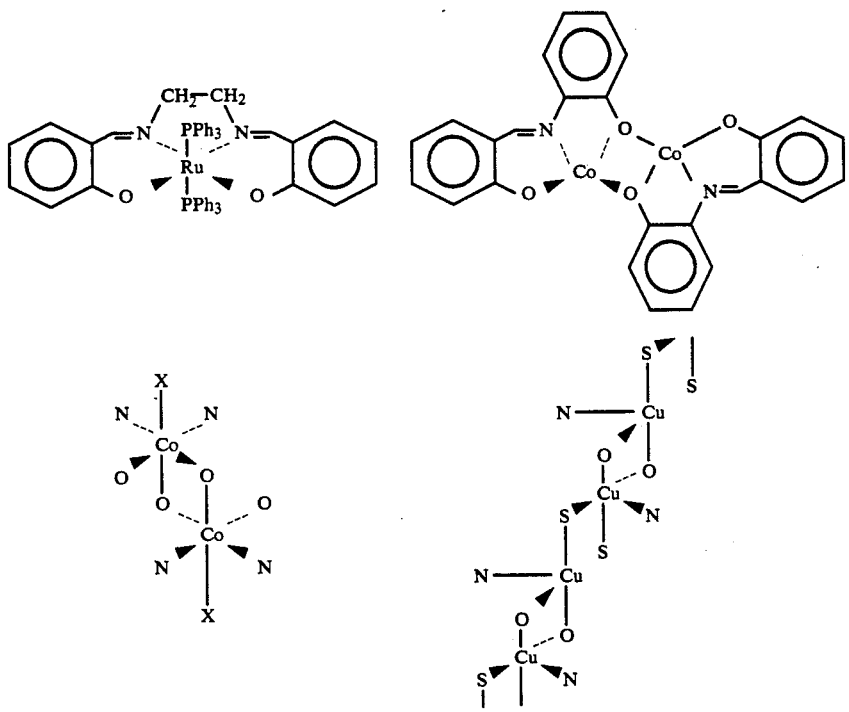

The concentration of the metal macrocyclic complexes in the present contacting step may vary depending, for example, on the specific reactants and amounts of same being employed, on the specific solvent, if any, and amount of same being employed, on the specific metal included in the complex, on the specific ligand included in the complex and/or on the contacting conditions. Such concentration is preferably in the range of about 0.01% to about 5%, more preferably about 0.05% to about 2%, by weight of the total reactants, solvent, if any, halogen component, if any, and catalyst composition present during said contacting.

The contacting preferably takes place in the presence of at least one halogen component in an amount effective to facilitate the formation of the carbamate. Such halogen component, preferably selected from chlorine components, bromine components, iodine components and mixtures thereof, more preferably from iodine components and mixtures thereof, in combination with the presently useful metal macrocyclic complex or complexes provides increased yields of carbamate relative to contacting without the presence of such halogen components.

Any halogen-containing material may be employed provided that an effective amount of halogen component, e.g., halide ion, is present during the contacting step of the present invention. The halogen-containing compounds which can be used as halogen component sources include alkali metal halides, alkaline earth metal halides, onium halides, compounds capable of forming onium halides at the contacting conditions, oxo acids of halogen atoms and their salts, complex compounds containing halogen ions, organic halides and halogen molecules.

Exemplary alkali metal halides and alkaline earth metal halides include single salts such as sodium fluoride, cesium fluoride barium chloride, rubidium chloride, cesium chloride, potassium chloride, rubidium chloride, cesium chloride, magnesium chloride, calcium chloride, strontium chloride, barium chloride, lithium bromide, sodium bromide, rubidium bromide, cesium bromide, magnesium bromide, strontium bromide, batium bromide, lithium iodide, sodium iodide, potassium iodide, rubidium iodide, cesium iodide, magnesium iodide, calcium iodide, strontium iodide, and barium iodide, calcium iodide, strontium iodide, and barium iodide, double salts such as sodium magnesium chloride, potassium magnesium chloride, potassium calcium chloride and potassium magnesium bromide, and polyhalides such as potassium bromofluoride, potassium iodochloride, rubidium iodochloride, cesium iodochloride, cesium iodochlorobromide, rubidium iodochlorobromide, potassium iodobromide, cesium iodobromide and rubidium iodobromide.

The term onium halide means a compound containing an element having a lone pair of electrons in which a proton or another cation type reagent is bonded to the lone pair of electrons to increase one covalent bond valency of the element having the lone pair of electrons to become a cation, and having a halogen anion electrovalently bound as the counter ion.

Exemplary onium halides include ammonium compounds of the formula $(R^2R^3R^4R^5N+)X^-$, phosphonium compounds having the formula $(R^2R^3R^4R^5P+)X^-$, arsonium compounds having the formula $(R^2R^3R^4R^5As)X$, stibonium compounds having the formula $(R^2R^3R^4R^5Sb)X$, oxonium compounds having the formula $(R^2R^3R^4O+)X^-$, sulfonium compounds having the formula $(R^2R^3R^4S+)X^-$, oxysulfonium compounds having the formula $[R^2R^3R^4S+(O)]X^-$, selonium compounds having the formula $(R^2R^3R^4Se+)X^-$, telluronium compounds having the formula $(R^2R^3R^4Te+)X^-$, stannonium compounds $(R^2R^3R^4Sn+)X^-$ and idonium compounds having the formula $(R^2R^3I+)X^-$. In these formulae, $R^2$, $R^3$, $R^4$ and $R^4$ each independently represents a hydrogen atom or a group selected from the group consisting of aliphatic groups, aromatic groups, alicyclic groups, arylaliphatic groups and heterocyclic groups which may sometimes be a constituent of a ring containing an element having a lone pair of electrons; and X represents a halogen atom selected from the group consisting of F, Cl, Br and I. Compounds having two or more of such onium groups in the molecule and further polymers containing such onium groups in the molecule and further polymers containing such onium groups in the main chain or a side chain thereof may also be employed.

Such onium halides where a halogen is an anion can readily be obtained by the reaction of a hydrogen halide or an organic halide with the counterpart amine, nitrogen-containing compound, stibine compound, oxy compound, sulfide compound, sulfoxide compound, selenide compound or telluride compound. These onium halides may be formed either outside the reaction system or in the reaction system. Furthermore, the onium halides prepared according to other methods may also be available and they may be formed in the reaction system according to other methods.

The concentration of the halogen component in the present contacting step may vary depending, for example, on the specific reactants and amounts of same being employed, on the specific solvent, if any, and amount of same being employed, on the specific metal included in the metal macrocyclic complex, on the specific ligand included in the complex, on the specific halogen component being employed and/or on the contacting conditions. Such concentration is preferably in the range of about 0.05% to about 10%, more preferably about 0.1% to about 5%, by weight of the total reactants, solvent, if any, halogen component, and catalyst composition present during said contacting.

The primary amine components and secondary amine components which can be used as the starting material in this invention are selected from compounds having at least one amino group represented by the following formulae in one molecule:

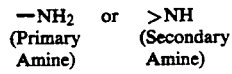

wherein the one line or the two lines bonded to a nitrogen atom indicate bonds between the nitrogen atom and other atoms or groups, such as a hydrogen atom, a halogen atom, an alkali metal, a hydroxyl group, an amino group, a hydrocarbyl group, for example, an aliphatic group, an alicyclic group, an aromatic group, an arylaliphatic group and a heterocyclic group, and a substituted hydrocarbyl group.

In the secondary amines, the nitrogen atom may itself be an element forming a ring as in pyrrole, piperidine, piperazine and morpholine.

Exemplary primary amines which can be used include ammonia; aliphatic primary monoamines such as methylamine, ethylamine, propylamine (respective isomers), butylamine (respective isomers), pentylamine (respective isomers), hexylamine (respective isomers) and dodecylamine (respective isomers); aliphatic primary diamines such as ethylenediamine, diaminopropane (respective isomers) and diaminobutane (respective isomers), diaminopentane (respective isomers), diaminohexane (respective isomers) and diaminodecane (respective isomers), aliphatic primary triamines such as 1,2,3-triaminopropane, triaminohexane (respective isomers), triaminononane (respective isomers) and triaminododecane (respective isomers) alicyclic primary mono- and poly-amines such as cyclopropylamine, cyclobutylamine, cyclopentylamine, cyclohexylamine, diaminocyclobutane, diaminocyclohexane (respective isomers); and trimaminocyclohexane (respective isomers); arylaliphatic primary mono- and poly-amines such as benzylamine, di(aminomethyl) benzene (respective isomers), aminomethylpyridine (respective isomers), di(aminomethyl) pyridine (respective isomers), aminomethylnaphthaline pyridine (respective isomers), aminomethylnaphthaline (respective isomers) and di(aminomethyl)naphthalene (respective isomers); and heterocyclic primary amines such as aminofuran (respective isomers), aminotetrahydrofuran (respective isomers), aminothiophene (respective isomers), aminopyrrole (respective isomers), aminopyrrolidine (respective isomers); aromatic primary amines such as aniline, diaminobenzene (respective isomers), triaminobenzene (respective isomers), tetraaminobenzene (respective isomers), aminotoluene (respective isomers), diaminotoluene (respective isomers), aminopyridine (respective isomers), diaminopyridine (respective isomers), aminonaphthalene (respective isomers), diaminonaphthalene (respective isomers), triaminonaphthalene (respective isomers) tetraaminonaphthalene (respective isomers) and respective isomers of monoamines, diamines, triamines and tetraamines of diphenyl compounds represented by the formula

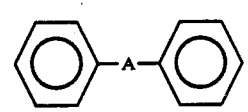

wherein A represents a chemical bond or a divalent group selected from the group consisting of —O—, —S—, —SO$_2$—, —CO—, —CONH—, —COO—, —C(R$^6$)(R$^7$)— and —N(R$^6$)— wherein R$^6$ and R$^7$ each is a hydrogen atom, an aliphatic group or an alicyclic group.

In these aromatic primary amines, at least one hydrogen substituent such as a halogen atom, a nitro group, a cyano group, an alkyl group, an alicyclic group, an aromatic group, an aralkyl group, an alkoxy group, a sulfoxide group, a sulfone group, a carbonyl group, an ester group and an amino group.

Of these aromatic amines, aniline, 2,4- and 2,6-diaminotoluene, chloroaniline (respective isomers), dichloroaniline (respective isomers), 4,4'- and 2,4'-diaminodiphenylmethane and 1,5-diaminonaphthalene are preferred.

A particularly useful class of primary amines are those selected from

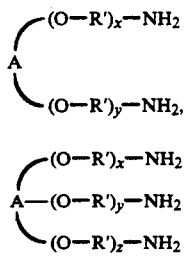

wherein each R' is independently selected from hydrocarbyl groups and substituted hydrocarbyl groups; each x, y and z is independently selected from integers having an average value in the range of 0 to about 1000, preferably in the range of 0 to about 150 and more preferably in the range of 0 to about 50 provided that no more than one of x, y and z is 0, and A is selected from hydrocarbyl groups and substituted hydrocarbyl groups. Each R' is preferably independently selected from alkyl groups, more preferably from alkyl groups having 1 to 3 carbon atoms, and still more preferably from ethyl and isopropyl. These amines can be produced using conventional procedures, such as, for example, reacting a polyalkanediol, e.g., polybutanediol, with sufficient alkylene oxide, e.g., propylene oxide, to form an adduct which is then reacted with ammonia or ammonium hydroxide in the presence of a suitable reductive amination catalyst to produce the desired amine. One such procedure is described in Watts, Jr. et al U.S. Pat. No. 4,148,819, which is incorporated herein in its entirety by reference.

These amines may often be referred to as polyoxyalkylene amines, e.g., diamines and triamines. A number of such amines are sold by Texaco Chemical Co. under the trademark JEFFAMINE ®.

For example, amines sold as JEFFAMINE ®D-series products have the formula:

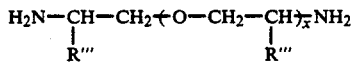

wherein each R''' is independently selected from hydrogen and methyl, and x is an integer having an average value of about 1 to about 60.

Representative polyoxypropylene diamines having the above-noted diamine structure with y equal to zero are as follows:

JEFFAMINE ® D-230, x=2-3
JEFFAMINE ® D-400, x=5-6
JEFFAMINE ® D-2000, x=about 33
JEFFAMINE ® D-4000, x=about 60

Representative polyoxypropylene triamines which are useful in the present invention and have the above-noted triamine structure are as follows:

JEFFAMINE ® T-403, Average molecular weight=440, A derived from trimethylolpropane
JEFFAMINE ® T-3000, Average molecular weight=3000,
A derived from glycerine
JEFFAMINE ® T-5000, Average molecular weight=5000, A derived from glycerine Exemplary secondary amines which can be used in this invention include aliphatic secondary amines such as dimethylamine, diethylamine, dipropylamine (respective isomers), dibutylamine (respective isomers), dipentylamine (respective isomers), dihexylamine (respective isomers), ethylmethylamine, ethylpropylamine (respective isomers), butylmethylamine (respective isomers) and ethylhexylamine (respective isomers); alicyclic secondary amines such as dicyclopropylamine, dicyclohexylamine and methylcyclohexylamine, aromatic secondary amines such as N-methylaniline, N-ethylaniline, N,N'-diphenylmethanediamine, N,N'-dimethylphenylenediamine (respective isomers), N-methylnaphthylamine (respective isomers) and dinaphthylamine (respective isomers) arylaliphatic secondary amines such as dibenzylamine, ethylbenzylamine and diphethylamine; heterocyclic secondary amines such as difuranylamine and dithiophenylamine; and cyclic secondary amines such as pyrrolidine, pyrrole, 3-pyrrolidone, indole, carbazole, piperidine, piperazine, B-piperidone, y-piperidone, imidazole, pyrazole, triazole, benzimidazole, morpholine and 1,3-oxazine.

In these primary amines and secondary amines, one or more hydrogens of the organic group bonded to the nitrogen may be substituted by a substituent such as a lower aliphatic group, an amino group, a carboxyl group, an ester group, an alkoxy group, a cyano group, a halogen atom, a nitro group, a urethane group, a sulfoxide group, a sulfone group, a carbonyl group, an amide, an aromatic group and arylaliphatic group. Further, these primary amines and secondary amines may also have an unsaturated bond.

In this invention it is also possible to use compounds having an amino group and a hydroxyl group in the molecule such as ethanolamine, propanolamine and o-aminobenzyl alcohol. In such a case, cyclic urethanes or carbamates can be produced.

In order to produce carbamates to be employed as starting materials for the preparation of isocyanate compounds, it is preferred that the primary amines are used.

The urea component which can be employed as the starting material in this invention is selected from compounds having at least one urea bond represented by the following formula in one molecule

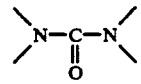

wherein the two lines bonded to a nitrogen atom indicate bonds between the nitrogen atom and other atoms or groups such as a hydrogen atom, a halogen atom, a hydrocarbyl group, for example, an aliphatic group, an alicyclic group, an aromatic group, an arylaliphatic group and a heterocyclic group, a substituted hydrocarbyl group and the nitrogen atom or the urea bond by itself may be an element forming a ring.

Suitable examples of such urea compounds which can be employed in this invention include non-substituted urea, i.e., urea, and mono-, di-, tri- or tetra-substituted ureas.

Exemplary mono-substituted ureas include aliphatic mono-substituted ureas such as methylurea, ethylurea, propylurea (respective isomers), butylurea (respective isomers) and hexylurea (respective isomers), alicyclic mono-substituted ureas such as cyclopropylurea, cyclobutylurea and cyclohexylurea; arylaliphatic mono-substituted ureas such as benzylurea and beta-phenethylurea; heterocyclic mono-substituted ureas such as furanylurea and thiophenylurea; aromatic mono-substituted ureas such as phenylurea, tolyureas and naphthylureas.

Exemplary di-substituted ureas include aliphatic N, N-di-substituted ureas such as N,N-dimethylurea, N,N-diethylurea. N,N-di-n-propylurea, N,N-di-n-butylurea, N,N-di-n-hexylurea, N-ethyl-N-methylurea and N-ethyl-N-n-butylurea; alicyclic N, N-di-substituted ureas such as N,N-dicyclopropylurea, N,N-dicyclobutylurea, N,N-dicyclohexylurea, N-cyclopropyl-N-methylurea and N-cyclohexyl-N-ethylurea; arylaliphatic N,N-di-substituted ureas such as N,N-dibenzylurea and N-benzyl-N-methylurea; heterocyclic N,N-di-substituted ureas such as N,N-difuranylurea, N,N-dithiophenylurea and N-furanyl-N-methylurea; aromatic N,N-di-substituted ureas such a N,N-diphenylurea, N,N-p-tolyurea, N,N-o-tolyurea, N,N-m-tolyurea, N,N-di-alpha-naphthylurea, N,N-di-beta-naphthylurea, N-phenyl-N-methylurea, N-phenyl-N-p-tolylurea, N-beta-naphthyl-N-benzylurea and N-phenyl-N-cyclohexylurea; aliphatic N,N'-di-substituted ureas such as N,N'-dimethylurea, N,N'-diethylurea, N,N'-di-n-propylurea, N,N'-di-n-butylurea, N,N'-di-n-hexylurea, N-ethyl-N'-methylurea, N-ethyl-N'-n-butylurea and N-n-hexyl-N'-methylurea; alicyclic N,N'-di-substituted ureas such as N,N'-dicyclopropylurea, N,N'-dicyclobutylurea, N,N'-dicyclohexylurea, N-cyclopropyl-N'-methylurea and N-cyclohexyl-N'methylurea; heterocyclic N,N'di-substituted ureas such as N,N'-difuranylurea and N,N'-dithiophenylurea; aromatic N,N'-di-substituted ureas such as N,N'-diphenylurea, N,N'-di-p-tolylurea. N,N'-di-o-tolyurea, N,N'-di-m-tolyurea, N,N'-di-alpha-naphthylurea, N,N'-di-beta-napthylurea, N-phenyl-N'-p-tolyurea. N-phenyl-N'-alpha-naphthylurea, N-phenyl-N'-ethylurea, N-alpha-naphthyl-N-benzylurea and N-phenyl-N'-cyclohexylurea; and ureas of cyclic nitrogen-containing compounds such as piperidylurea and pyrrolidinylurea, Exemplary tri-substituted ureas include aliphatic tri-substituted ureas such as trimethylurea, triethylurea, tri-n-propylurea, tri-n-butylurea, tri-n-hexylurea, N,N-dimethyl-N, -ethylurea, N,N-diethyl-N'-n-butylurea and N-methyl-N-ethyl-N'-n-butylurea; alicyclic tri-substituted ureas such as tricyclopropylurea, tricyclohexylurea, N,N'-dicyclohexyl-N'-methylurea, N-cyclohexyl-N'-methylurea, N-cyclohexyl-N-ethyl-N'-n-butylurea and N,N-diethyl-N'-cyclobutylurea, heterocyclic tri-substituted ureas such as trifuranylurea, trithiophenylurea and N,N'-difuranyl-N-methylurea; aromatic tri-substituted ureas such as triphenylurea, tri-p-tolyurea, tri-o-tolyurea, tri-m-tolyurea, tri-alpha-naphthylurea, tri-beta-naphthylurea, N,N-diphenyl-N'-methylurea, N,N'-diphenyl-N'-methylurea, N, N'-diphenyl-N-cyclohexylurea, N,N-dimethyl-N'-phenylurea, N-phenyl-N-ethyl-N'-benzylurea; and ureas of N-substituted cyclic nitrogen-containing compounds such as N-ethylpiperidylurea and N-methylpyrodinylurea.

Exemplary tetra-substituted ureas include aliphatic tetra-substituted ureas such as tetramethylurea, tetra-thylurea, tetra-n-propylurea, tetra-n-hexylurea, diethyldimethylurea and ethyltrimethylurea; alicyclic tetrasubstituted ureas such as tetracyclopropylurea, tetracyclohexylurea, dicylohexyldiethylurea and cyclobutyltrimethylurea; arylaliphatic tetra-substituted ureas such as tetrabenzylurea, tribenzylmethylurea, dibenzyldiethylurea and benzyltrimethylurea; heterocyclic tetrasubstituted ureas such as tetrafuranylurea, tetrathiophenylurea and furanyltrimethylurea; aromatic tetrasubstituted ureas such as tetraphenylurea, tetra-p-tolyurea, tetra-m-tolyurea, tetra-o-tolyurea, tetra-alpha-naphthylurea, tetra-beta-naphthylurea, methyltriphenylurea , diethyldiphenylurea, dicyclohexyldiphenylurea, alpha-naphthyltriethylurea and beta-naphthyltriethylurea, cyclic ureas in which a urea bond is the member constituting a ring such as 2-imidazoline, 2-imidazolidone, biotin, hydantoin, N, N'-hexamethylurea, parabanic acid and benzimidazole; compounds having at least two urea bonds in the molecule such as N,N'-dimethylcarbamoylhexamethylenediamine and N,N'-diphenylcarbamoylhexamethylenediamine; and polymeric ureas having units of the following formula in the molecule

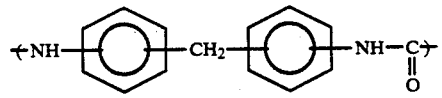

In these substituted urea compounds at least one hydrogen in the substituent may be substituted with a lower aliphatic group, an amino group, a carboxyl group, an ester group, an alkoxy group, a cyano group, a halogen atom, a nitro group, a urethan group, a sulfoxide group, a sulfone group, a carbonyl group, an amido group, an aromatic group or an arylaliphatic group.

As is apparent from the above, any of a wide variety of urea compounds may be utilized in this invention. In carrying out the reaction using a primary or secondary amine, the counterpart urea compound may sometimes be present as an intermediate in the reaction system but this urea compound is preferably converted to a carbamate.

According to this invention, the primary amine component, the secondary amine component and the urea component may be used alone or in various mixtures.

The organic hydroxyl component which can be used in this invention include aliphatic and aromatic compounds such as monohydric or polyhydric alcohols or monohydric or polyhydric phenols. Such alcohols include, for example, straight or branched monohydric or polyhydric alkanols or alkenols having 1 to about 20 carbon atoms per molecule, monohydric or polyhydric cycloalkanols or cycloalkenols having 3 to about 20 carbon atoms per molecule and monohydric or polyhydric aralalkylalcohols having 7 to about 20 carbon atoms per molecule. Further, these alcohols may also have a substituent such as a halogen atom, a cyano group, an alkoxy group, a sulfoxide group, a sulfone group, a carbonyl group, an ester group and an amide group.

Exemplary alcohols include aliphatic alcohols such as methanol, ethanol, propanol (respective isomers), butanol (respective isomers), pentanol (respective isomers), hexano (respective isomers) heptanol (respective isomers), octanol (respective isomers), nonyl alcohol (respective isomers), decyl alcohol (respective isomers), undecyl alcohol (respective isomers) lauryl alcohol (respective isomers), tridecyl alcohol (respective isomers), tetradecyl alcohol (respective isomers) and pentadecyl alcohol (respective isomers); cycloalkanols such as cyclohexanol and cycloheptanol; alkylene glycol monoethers such as ethylene glycol monomethylether, ethylene glycol monoethylether, diethylene glycol monomethylether, diethylene glycol monoethylether, triethylene glycol monomethylether, triethylene glycol monoethylether, propylene glycol monomethylether and propylene glycol monoethylether, polydric alcohols such as ethyl glycol, propylene glycol, diethylene glycol, dipropylene glycol, glycerine, hexanetriol and trimethylolpropane, and aralkyl alcohols such as benzyl alcohol.

Exemplary phenols include phenol, various alkylphenols, various alkoxyphenols, various halogenated phenols, dihydroxybenzene, 4,4-dihydroxydiphenylmethane, bisphenol-A and hydroxynaphthalene.

Of the above described organic hydroxyl compounds, aliphatic monoalcohols having 1 to about 10 carbon atoms per molecule, alicyclic monoalcohols having 3 to about 10 carbon atoms per molecule or aralkyl monoalcohols having 7 to about 15 carbon atoms per molecule are preferred.

In the case of the reaction using a primary or secondary amine component, the amount of the alcohol or phenol employed is typically at least one mole per amino group of the primary or secondary amine. In the case of the reaction using a urea component, the amount of the alcohol or phenol employed is at least two moles per urea group of the urea component. In both cases the alcohol or phenol may be employed as a reaction medium. In such a case the amount of the alcohol or phenol is typically about 3 to 100 moles per amino group of the primary or secondary amine or per urea group of the urea component.

The carbon monoxide which can be employed as one starting material in this invention may be pure carbon monoxide or may contain other gases such as nitrogen, argon, helium, carbon dioxide, a hydrocarbon or a halogenated hydrocarbon. A small amount, for example, less than about 10% by mole of hydrogen based on carbon monoxide does not affect adversely the reaction using the catalyst system of this invention, and accordingly in this invention carbon monoxide containing such a small amount of hydrogen may be advantageously employed from the industrial viewpoint.

The amount of carbon monoxide which can be employed is typically at least one mole, preferably about 2 to about 100 moles per amino group of the primary or secondary amine component or per urea group of the urea component.

The oxidizing agent which can be used in this invention contains oxygen, in particular reducible oxygen. Molecular oxygen is preferred. The molecular oxygen may be diluted by nitrogen, e.g., air, and/or by the addition of one or more other gases which do not substantially interfere including gases such as argon, helium and carbon dioxide. In some cases the molecular oxygen-containing material may also contain a gas such as hydrogen, carbon monoxide, a hydrocarbon and a halogenated hydrocarbon.

In the process of this invention, it is preferred to use an excess of an organic hydroxyl component as the reaction medium. If necessary, other solvents which do not affect the reaction adversely may also be used. Exemplary solvents which can be employed include aromatic hydrocarbons such as benzene, toluene, xylene and mesitylene; nitriles such as acetonitrile and benzonitrile; sulfones such as sulforane, methylsulforane and dimethylsulforane, ethers such as tetrahydrofuran, 1,4-dioxyane and 1,2-dimethoxyethane, ketones such as acetone, methyl ethyl ketone; esters such as ethyl acetate and ethyl benzoate; and amides such as N,N-dimethylformamide, N-N-dimethylacetamide, N-methylpyrrolid one and hexamethylphosphoramide.

Further, it is also possible to use, as a solvent, a halogenated aromatic hydrocarbon which is one kind of the organic halide to be used as the promoter in this invention such as chlorobenzene, dichlorobenzene, trichlorobenzene, fluorobenzene, chlorotoluene, chloronaphthalene and bromonaphthalene, a halogenate aliphatic hydrocarbon or a halogenated alicyclic hydrocarbon such as chlorohexane, chlorocyclohexane, trichlorotrifluoroethene, methylene chloride and carbon tetrachloride.

The presence of water may cause side reactions such as the hydrolysis of carbamates and the water gas reaction of carbon monoxide and accordingly, it is possible to employ additives having a dehydrating action. Suitable examples of such additives include zeolites, orthoesters, ketals, acetals, enolethers and trialkyl orthoborates.

In the process of this invention, the reaction is carried out at a temperature in the range of about 80° C. to about 300° C., preferably about 120° C. to about 220° C. The reaction pressure is typically in the range of about 10 psi to about 5000 psi, preferably about 200 psi, to about 3000 psi. The reaction time which may vary depending on the reaction system employed and other reaction conditions chosen is typically in the range of about one minute to about 10 hours.

The reaction of this invention can be carried out either batch-wise or continuously by removing continuously the reaction mixture from the reaction system while continuously feeding the reactants into the reaction system.

After the contacting step or steps, the carbamatecontaining material may be worked up in any manner known to those in the art, such as distilling off volatile materials. It is particularly desirable that such distillation be carried out after insoluble constituents, such as insoluble catalysts, have been filtered off. In cases where the carbamatecontaining material is worked up by distillation, the product carbamate often accumulates as the final fraction collected or as the distillation residue. Any of the reactants present in the end product may be separated by techniques known to those in the art. One such separation technique is taking up the distillation residue in a suitable selective solvent and subsequently filtering off the unreacted reactant.

The products obtained by the process according to the present invention represent valuable starting materials for preparing the corresponding isocyanates. Preparation of organic isocyanates from the carbamates of the present invention is preferably carried out by thermally splitting the carbamates into the isocyanate and the hydroxy organic component on which they are based by techniques known to those in the art.

The thermal decomposition of the present carbamates to the corresponding isocyanates is preferably conducted by contacting the carbamate or carbamates at an elevated temperature, more preferably in the range of about 150° C. to about 600° C., for a time sufficient, more preferably in the range of about 0.1 hours to about 5 hours or more, to produce the corresponding isocyanate or isocyanates and hydroxy organic compound or compounds from which the carbamate or carbamates were derived.

One or more suitable catalysts, such as those conventionally employed to thermally decompose carbamates to isocyanates, may be employed to promote the rate of formation of and/or selectivity to the isocyanate or isocyanates. Examples of carbamate decomposition catalysts include, but are not limited to, metals belonging to Groups IA, IB, IIA, IIB, IIIA, IIIB, IV A, IV B, VA, VB, VIB, VIIB and VIII of the Periodic Table and organic and inorganic compounds thereof; Lewis acids; mixtures thereof and the like. The catalyst concentration may vary widely and depend, for example, on the specific catalyst being employed, the specific carbamate or carbamates to be decomposed, and the specific decomposition conditions being employed. Often, the catalyst is present in an amount in the range of about 0.01% to about 10% by weight of the carbamate or carbamates to be decomposed.

Suitable solvents may also be employed in the carbamate decomposition step. If solvents are used, they should be substantially inert under decomposition conditions with respect to the reactants and products which are present, and should have a different boiling point than the isocyanate and other products. Examples of useful solvents include, but are not limited to, aliphatic hydrocarbons such as higher alkanes; alicyclic hydrocarbons such as fractions of the napththene series; aromatic and substituted aromatic hydrocarbons such as naphthenes and alkyl benzenes; aliphatic and aromatic ketones; sulfone; esters; ethers; mixtures thereof and the like. The amount of solvent used may vary widely, and depends for example on the specific carbamate or carbamates to be decomposed, the specific solvent being employed and the specific decomposition conditions being employed. Excessive amounts of solvent are to be avoided so that the products can be effectively and efficiently separated from the solvent.

Sub-atmospheric, atmospheric and/or super-atmospheric pressure may be employed in the carbamate decomposition step. The product isocyanate or isocyanates can be recovered from the product mixture using conventional techniques, such as distillation, extraction, filtration and the like.

The following non-limiting examples illustrate certain aspects of the present invention.

EXAMPLE 1 butylamine, 0.20 g of CoTPP [TPP=mesotetraphenylporphinato dianion] and 1.0 g of NaI are charged to a 300 ml Hastelloy ®C autoclave reactor along with 40 g of ethanol. The reactor is then sealed, purged with nitrogen, and pressurized with 80 psi of oxygen and 1520 psi of carbon monoxide. With constant stirring with a magnetic drive, the mixture in the reactor is heated to 200° C. The temperature is then kept constant for 3 hours. Afterwards, the reactor is cooled to room temperature and depressurized. The contents of the reactor are analyzed by gas chromatography. It is shown that all of the amine reacted and that 5.7 g of ethyl N-tert-butylcarbamate formed. The yield of such carbamate is 96% on the amine charged.

EXAMPLE 2

Example 1 is repeated except that no NaI is used. It is found that 30% of the amine reacted and 0.69 g of ethyl N-tert-butylcarbamate is formed.

EXAMPLE 3

1.5 g of tert-butylamine, 0.20 g CoTPP and 1.0 % NaI are charged to the reactor along with 40 g of ethanol. After the reactor is sealed and purged with nitrogen, it is pressurized with 50 psi of oxygen and 950 psi of carbon monoxide. The reactor is then heated to 200° C. for 3 hours. After being cooled to room temperature, the reactor is depressurized. The reactor contents are analyzed by gas chromatography and shown to contain 2.7 g of ethyl N-tert-butylcarbamate. The yield of such carbamate is 97% based on the amine charged.

EXAMPLE 4

A procedure similar to Example 1 is used. 3.0 g of tert-butylamine, 0.20 g of Co(Pc) [Pc=phthalocyanine dianion] and 1.0 g of NaI are initially charged to the reactor along with 40 g of ethanol. It is found that 78% of the amine reacted and 4.4 g of ethyl N-tert-butylcarbamate is formed. The yield of such carbamate based on the amine reacted was 96%.

EXAMPLE 5

A procedure similar to Example 1 is used except that the reaction temperature is 160° C. 3.0 g of tert-butylamine, 0.2 g of Co(Salen) [Salen ™ N,N'-bis(-salicylidene)ethylenedaimine] and 1.0 g of NaI are initially charged to the reactor along with 40 g of ethanol. It is found that all of the amine reacted and 6.0 g of ethyl N-tert-butylcarbamate is formed. The yield of such carbamate based on the amine charged is 99%.

EXAMPLE 6

A procedure similar to Example 1 is used. 3.0 g of tert-butylamine, 0.20 g of Cu(Pc) and 1.0 g of NaI are initially charged to the reactor. It is found that 63% of the amine reacted and 3.0 g of ethyl N-tert-butylcarbamate is formed. The yield of such carbamate based on the amine reacted is 81%.

EXAMPLE 7

A procedure similar to Example 1 is used. 3.0 g of tert-butylamine, 0.20 g of CoTPP and 1.0 g of LiI are initially charged to the reactor along with 40 g of ethanol. It is found that all of the amine reacted and 5.8 g of ethyl N-tert-butylcarbamate is formed. The yield of such carbamate based on the amine charged is 98%.

EXAMPLE 8

A procedure similar to Example 1 is used. 3.0 g of tert-butylamine, 0.20 g of CoTPP and 1.0 g of KI are initially charged to the reactor along with 40 g of ethanol. It is found that all of the amine reacted and 5.4 g of ethyl N-tert-butylcarbamate is formed. The yield of such carbamate based on the amine charged is 93%.

EXAMPLE 9

A procedure similar to Example 1 is used. 3.0 g of tert-butylamine, 0.20 g of CoTPP and 1.0 g of NaBr are initially charged to the reactor along with 40 g of ethanol. It is found that 75% of the amine reacted and 2.3 g of ethyl N-tert-butylcarbamate formed. The yield of such carbamate based on the amine reacted is 52%.

EXAMPLE 10

A procedure similar to Example 1 is used. 3.0 g of tert-butylamine, 0.20 g of CoTPP, 1.0 g of NaI and 50 g of 2,2,2-trifluroethanol are initially charged to the reactor. It is found that all of the amine reacted and 7.8 g of 2,2,2-trifluorethyl N-tert-butylcarbamate is formed. The yield of such carbamate based on the amine charged is 95%.

EXAMPLE 11

A procedure similar to Example 1 is used. 3.0 g of tert-butylamine, 0.20 g of CoTPP, 1.0 g of NaI and 40 g of methanol are initially charged to the reactor. It is found that all of the amine is reacted and 2.4 g of methyl N-tert-butylcarbamate is formed. The yield of such carbamate based on the amine charged is 61%.

EXAMPLE 12

3.0 g of cyclohexylamine, 0.20 g of CoTPP and 1.0 g of NaI are charged to the reactor along with 40 g of ethanol. After the reactor is sealed and purged with nitrogen, it is pressurized with 80 psi of oxygen and 920 psi of carbon monoxide. The reactor is then heated to 200° C. for 3 hours. After being cooled to room temperature, the reactor is depressurized. The contents are analyzed by gas chromatography and shown to contain 5.2 g of ethyl N-cyclohexyl-carbamate. The yield of such carbamate was 98% based on the amine charged.

EXAMPLE 13

3.0 g of cyclohexylamine, 0.20 g of Co(Salen) and 1.0 g of NaI are charged to the reactor along with 40 g of ethanol. After the reactor is sealed and purged with nitrogen, it is pressurized with 80 psi of oxygen and 1520 psi of carbon monoxide. The reactor is then heated to 160° C. for 3 hours. After being cooled to room temperature, the reactor is depressurized. The contents of the reactor are analyzed by gas chromatography and shown to contain 0.3 g of unreacted cyclohexylamine and 4.1 g of ethyl N-cyclohexyl-carbamate. The yield of such carbamate is 89% based on the amine reacted.

EXAMPLE 14

1.7 g methylamine is dissolved in 40 g of ethanol and the solution is charged to the reactor along with 0.20 g of CoTPP and 1.0 g of NaI. After the reactor is sealed and purged with nitrogen, it is pressurized with 80 psi of oxygen and 920 psi of carbon monoxide. The reactor is then heated to 200° C. for 3 hours. After being cooled to room temperature, the reactor is depressurized. The contents of the reactor are analyzed by gas chromatography and shown to contain 5.4 g of ethyl N-methylcarbamate. The yield of such carbamate is 96% based on the amine charged.

EXAMPLE 15

A procedure similar to Example 1 is used. 3.0 g of m-toluidine, 0.20 g of CoTPP, 1.0 g of NaI and 40 g of ethanol are charged to the reactor initially. It is shown by gas chromatography that 86% of the amine is reacted and ethyl-N-m-toyl-carbamate is formed in 99% yield based on the amine reacted.

EXAMPLE 16

A procedure similar to Example 1 is used. 3.0 g of aniline, 0.20 g of CoTPP, 1.0 g of NaI and 40 g of ethanol are charged to the reactor initially. It is shown by gas chromatography that 80% of the amine is reacted and ethyl N-phenyl carbamate is formed in 52% yield based on the amine reacted. Diphenyl urea (35%) and N-ethylaniline (4%) are the other main products.

EXAMPLE 17

A procedure similar to Example 1 is used. 3.0 g of aniline, 0.08 g of Rh(TPP)Cl, 1.0 g of NaI and 40 g of ethanol are charged to the reactor initially. It is found that 73% of the aniline is reacted and ethyl N-phenyl carbamate is formed in 77% yield based on the amine reacted. The yield of N-ethylaniline is 14% based on the amine reacted.

EXAMPLE 18

A procedure similar to Example 1 is used. 3.0 g of aniline, 0.2 g of Pd(TPP), 1.0 g of NaI and 40 g of ethanol is charged initially to the reactor. It is found that 94% of the aniline is reacted and ethyl N-phenylcarbamate is formed in 83% yield based on the amine reacted. The yield on N-ethylaniline is 14% based on the amine reacted.

EXAMPLE 19

A procedure similar to Example 1 is used except that a reaction temperature of 160° C. is used. 3.0 g of aniline, 0.20 g of Co(Salen), 1.0 g of NaI and 40 g of ethanol are charged initially to the reactor. It is found that all the aniline is reacted. The yield of ethyl N-phenyl carbamate is 99% based on the amine charged.

EXAMPLE 20

A procedure similar to Example 1 is used. 3.0 g of aniline, 0.20 g of Co[tetrakis(4-methoxyphenyl)porphine], 1.5 g of NaI and 50 g of ethanol are initially charged to the reactor. It is found that 68% of the aniline is reacted. The yield of ethyl N-phenylcarbamate is 82% based on the amine reacted and the yield of N-ethylaniline is 14% based on the amine reacted.

EXAMPLE 21

A procedure similar to Example 1 is used. 3.0 g of aniline, 0.20 g of Co(phthalocyanine), 1.5 g of NaI and 50 g of ethanol are charged initially to the reactor. It is found that 77% of the aniline is reacted. The yield of ethyl N-phenylcarbamate is 84% based on the amine reacted and the yield of N-ethylaniline is 10% based on the amine reacted.

EXAMPLE 22

A procedure similar to example 1 is used. 3.0 g of aniline, 0.20 g of Cu(phthalocyanine), 1.5 g of NaI and 50 g of ethanol are charged initially to the reactor. It is found that 63% of the aniline based on the amine reacted was converted. The yield of ethyl N-phenylcarbamate is 42% based on the amine reacted and the yield of N-ethylaniline is 14% based on the amine reacted.

EXAMPLE 23

A procedure similar to Example 1 is used. 2.0 g of 1,6-hexanediamine, 0.20 g of CoTPP, 1.0 g of NaI and 40 g of ethanol are charged initially to the reactor. It is found that all the amine is reacted. The yield of diethyl hexamethylenedicarbamate is 95% based on the amine reacted.

EXAMPLE 24

A procedure similar to Example 1 is used. 3.0 g of isophorone diamine, 0.20 g of CoTPP, 1.0 g of NaI and 40 g of ethanol are charged initially to the reactor. It is found that all the amine is reacted. The yield of diethyl isophorone dicarbamate is 70% based on the amine reacted.

EXAMPLE 25

A procedure similar to Example 1 is used. 3.0 g of isophorone diamine, 0.20 g of CoTPP, 1.0 g of KI and 40 g of ethanol are charged initially to the reactor. It is found that all the amine is reacted. The yield of diethyl isophorone dicarbamate is 73% based on the amine charged.

EXAMPLE 26

A procedure similar to Example 1 is used. 3.0 g of 1,8-diamino-p-menthane, 0.20 g of CoTPP, 1.0 g of NaI and 40 g of ethanol are charged initially to the reactor. It is found that all the amine is reacted. The yield of the corresponding dicarbamate is 95% based on the amine charged.

EXAMPLE 27

A procedure similar to Example 1 is used. 3.0 g of 1,2-diamino-2-propane, 0.20 g of CoTPP, 1.0 g of NaI and 40 g of ethanol are charged initially to the reactor. It is found that all the amine is reacted. The yield of diethyl isophorone dicarbamate is 95% based on the amine charged.

EXAMPLE 28

A procedure similar to Example 1 is used. 3.0 g of 2,2-dimethyl-1-,3-proanediamine, 0.20 g of CoTPP, 1.0 g of NaI and 40 g of ethanol are charged initially to the reactor. It is found that all the amine is reacted. The yield of diethyl isophorone dicarbamate is 90% based on the amine charged.

EXAMPLE 29

A procedure similar to Example 1 is used. 3.0 g of 1,3-cyclohexylbis-(methylamine), 0.20 g of CoTPP, 1.0 g of NaI and 40 g of ethanol are charged initially to the reactor. It is found that all the amine is reacted. The yield of the corresponding dicarbamate is 90% based on the amine charged.

EXAMPLE 30

A procedure similar to Example 1 is used. 3.0 g of 3-ethoxypropylamine, 0.20 g of CoTPP, 1.0 g of NaI and 40 g of ethanol are charged initially to the reactor. It is found that all the amine is reacted. The yield of the corresponding diethyl dicarbamate is 95% based on the amine charged.

EXAMPLE 31

A procedure similar to Example 1 is used. 3.0 g of Jeffamine D-230, 0.20 g of CoTPP, 1.0 g of NaI and 40 g of ethanol are charged initially to the reactor. It is found that all the amine is reacted. The yield of the corresponding diethyl dicarbamate is estimated to be 70% based on the amine charged.

EXAMPLE 32

A procedure similar to Example 1 is used. 17 mmols of di-n-butylurea, 0.20 g of CoTPP, 1.5 g of NaI and 40 g of ethanol are charged initially to the reactor. The reactor is then sealed, purged with nitrogen and pressurized with 80 psi of oxygen and 1520 psi of carbon monoxide. The mixture in the reactor is heated to 200° C. and is then kept constant for 3 hours. It is found that 71% of the di-n-butylurea is reacted. The yield of ethyl N-n-butyl carbamate is 71% based on the di-n-butylurea reacted.

EXAMPLE 33

Example 32 is repeated except that 14 mmols of diphenylurea is used in place of the di-n-butyl urea. It is found that 80% of the diphenylurea is reacted. The yields of products, based on diphenyl urea reacted, are as follows:
ethyl N-n-phenyl carbamate 64%
N-ethyl aniline 7%
N, N-diethyl aniline 3%
aniline 5%

EXAMPLE 34

A procedure similar to Example 1 is used. 27 mmols of dicyclohexylurea, 0.25 g of CoTPP, 1.0 g of NaI and 40 g of ethanol are charged initially to the reactor. The reactor is then sealed, purged with nitrogen and pressurized with 80 psi of oxygen and 920 psi of carbon monoxide. The mixture in the reactor is heated to 180° C. and is then kept constant for 2 hours. It is found that all of the dicyclohexylurea is reacted. The yield of ethyl N-cyclohexyl carbamate is 95% based on the dicyclohexylurea charged.

While this invention has been described with respect to various specific examples and embodiments, it is to be understood that the invention is not limited thereto and that it can be variously practiced within the scope of the following claims.

We claim:

1. In a process for producing a carbamate which comprises contacting a first reactant selected from the group consisting of primary amine components, secondary amine components, urea components and mixtures thereof; carbon monoxide; at least one organic hydroxyl component and at least one oxygen-containing oxidizing agent at conditions effective to form a carbamate including the presence of a catalyst composition in an amount effective to promote the formation of a carbamate, the improvement wherein the catalyst composition comprises at least one redox cyclable metal macrocyclic complex selected from the group consisting of metal porphyrin or metal phthalocyanine including a metal selected from the metals of Group IIIa to Va and Group VIII of the Periodic Table and at least one iodine component is present in an amount effective to facilitate the formation of the carbamate.

2. The process of claim 1 wherein said at least one metal macrocyclic complex is substantially resistant to oxidative destruction at said conditions of said contacting.

3. The process of claim 1 wherein said at least one metal macrocyclic complex includes at least one metal selected from the group consisting of copper, zinc, mercury, thallium, tin, titanium, arsenic, antimony, bismuth, vanadium, chromium, molybdenum, tungsten, manganese, iron, cobalt, nickel and the platinum group metals.

4. The process of claim 1 wherein said at least one metal macrocyclic complex includes at least one metal selected from the group consisting of copper, cobalt, rhodium and palladium.

5. The process of claim 1 wherein said first reactant includes a primary amine component.

6. The process of claim 1 wherein said at least one oxygen-containing oxidizing agent is molecular oxygen.

7. In a process for producing an isocyanate which comprises contacting a first reactant selected from the group consisting of primary amine components, secondary amine components, urea components and mixtures thereof; carbon monoxide; at least one organic hydroxyl component and at least one oxygen-containing oxidizing agent at conditions effective to form a carbamate including the presence of a catalyst composition in an amount effective to promote the formation of a carbamate and contacting said carbamate at conditions effective to decompose the carbamate and form an isocyanate, the improvement wherein the catalyst composition comprises at least one redox cyclable metal macrocyclic complex selected from the group consisting of metal porphyrin and metal phthalocyanine including a metal selected from the metals of Group IIIa to Va and Group VIII of the Periodic Table and at least one iodine component is present in an amount effective to facilitate the formation of the carbamate.

* * * * *